United States Patent [19]

Atkinson et al.

[11] Patent Number: 5,397,694
[45] Date of Patent: Mar. 14, 1995

[54] PROTEASE INHIBITOR

[75] Inventors: Anthony Atkinson, Winterbourne Gunner; Asgar Electricwala, Salisbury; Roy T. Sawyer, Dyfed; Nils von Sicard, Fforesthall, all of Great Britain; Gerard Voerman, Ridderkerk, Netherlands

[73] Assignee: Merck Patent GmbH, Darmstadt, Germany

[21] Appl. No.: 768,226

[22] PCT Filed: Apr. 12, 1990

[86] PCT No.: PCT/NL90/00046
§ 371 Date: Oct. 24, 1991
§ 102(e) Date: Oct. 24, 1991

[87] PCT Pub. No.: WO90/12808
PCT Pub. Date: Nov. 1, 1990

[30] Foreign Application Priority Data

Apr. 14, 1989 [NL] Netherlands .................. 8900943

[51] Int. Cl.⁶ ............................................. A01N 1/00
[52] U.S. Cl. ...................................... 435/2; 424/94.6; 435/183; 435/218; 514/12; 514/902; 530/350
[58] Field of Search .............. 424/94.6; 435/183, 218; 530/350; 514/12, 902

[56] References Cited

PUBLICATIONS

Goldstein et al, Comp. Biochem. Physiol. B. Comp. Biochem. 84(1) pp. 117–124 1986.
Semeuller et al, Hope-Seyler's Z Physiol Chem 358(9) pp. 1105–1119 1977.

*Primary Examiner*—Robert A. Wax
*Assistant Examiner*—D. Schmickel
*Attorney, Agent, or Firm*—Darby & Darby

[57] ABSTRACT

This invention relates to a novel protease-inhibitor,— which we called GELIN—and to pharmaceutical and cosmetic preparations thereof, containing this compound. GELIN is an inhibitor of human and porcine leucocyte elastase and chymotrypsin. GELIN has specific antibiotic properties. It also relates to the novel use of EGLIN, another chymotrypsin-inhibitor in cosmetic preparations.

14 Claims, 12 Drawing Sheets

FIG. IIA
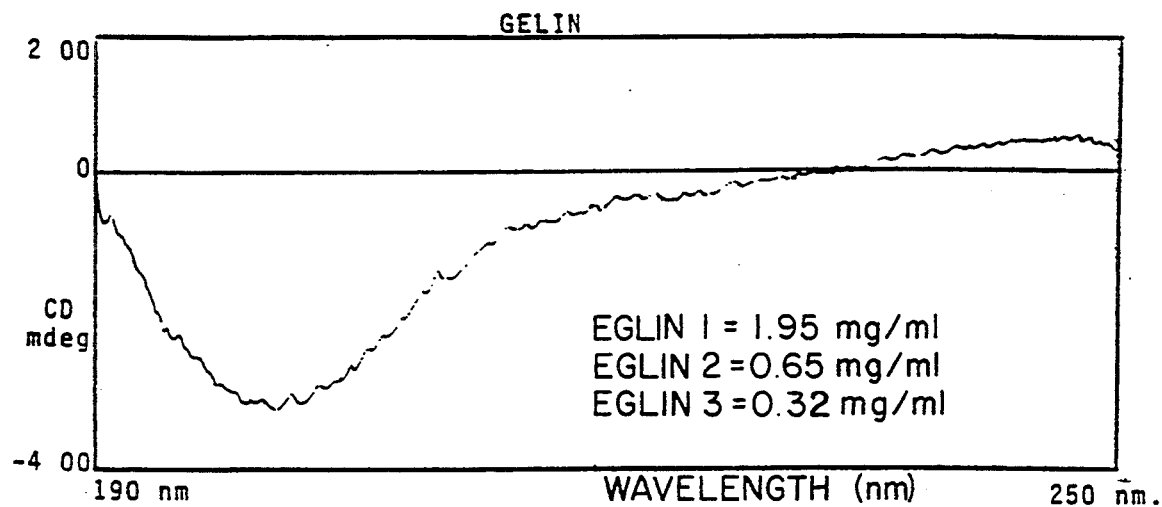
FIG. IIB
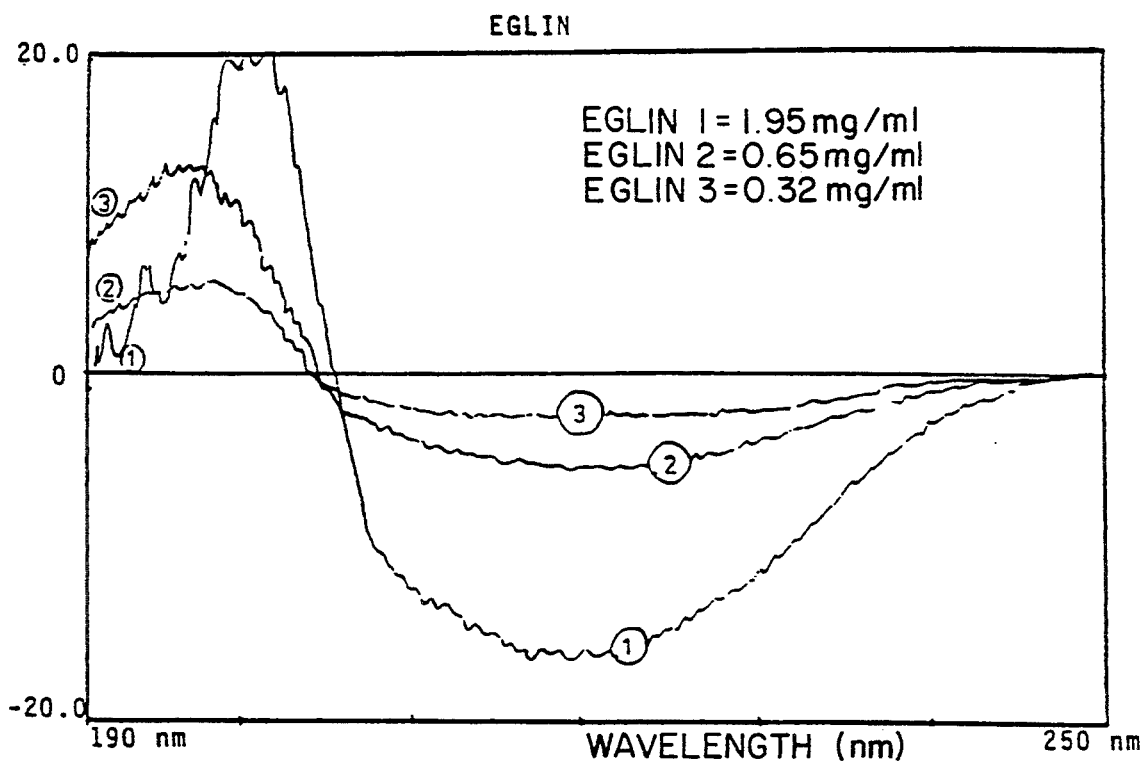

PROTEASE INHIBITOR

This invention relates to a novel protease-inhibitor-,—which we called Gelin—, and to pharmaceutical and cosmetic preparations thereof, containing this compound.

Gelin is an inhibitor of human and porcine leucocyte-elastase and chymotrypsin. Gelin has specific antibiotic properties. It also relates to the novel use of Eglin, another chymotrypsin-inhibitor in cosmetic preparations.

Several diseases, like emphysema, arthritis, gingivitis, periodontitis and other inflammatory conditions occur due to tissue destruction caused by the enzyme Elastase. Elastases are the only serine proteases which are capable of solubilising fibrous proteins like elastin and collagen. They are chiefly present in pancreas and in the azurophilic granules of neutrophil leucocytes. Under normal physiological conditions, the proteolytic activity of the enzyme is kept under check by the excess of inhibitors present in plasma and other secretions. However, under diseased state, local deficiency of inhibitor leads to an imbalance resulting in tissue destruction, the underlying cause of various inflammatory conditions.

As an example this situation is described for gingivitis. Disorders of neutrophil-functions are often associated with abnormalities and conditions of the host, e.g.: diabetes mellitus, Down's syndrome, icthyosis, rheumatoid arthritis, cyclic neutropenia, agranulocytosis, Chediak-Higashi syndrome. (Cianciola, L. J., et al., Nature (1977), 265:445-447; Cohen, W. D., et al., J. Period (1961), 32:159-168). Polymorphonuclear (PMN)-derived neutral proteases and/or bacterial toxins directly or indirectly attach supporting tissues in the dento-gingival area so as to cause inflammation (Janoff, A., J. Am. Path. (1972), 68:538-623; Weiss, S. J., New Engl. J. Med. (1989), 320-6:365-376; Henson, P. M., et al., J. Clin. Invest. (1987), 79:669-674; Campbell, E. J., et al., J. Clin. Invest. (1982), 70:845-852; Lehrer, R. I., et al., Ann. Int. Med. (1989), 109:127-142). Gingival crevicular fluid from inflamed gingival tissues contains high levels of hydrolytic enzymes. (Cimasoni, G., Monographs in Oral Science, Vol. 12.ed., H. M. Myers, Philadelphia, Pa., Karger (1983)). Oxygen radicals have both bacteriostatic as well as tissue-destructing activities. (Schalkwijk, J., Thesis, Nijmegen Holland (1986)). This tissue-destructing activity is at discussion. (Weiss, S. J., New Engl. J. Med. (1989), 320-6:365-376; Henson, P. M., et al., J. Clin. Invest. (1987), 79:669-674; Dakin, H. D., Br. Med. J. (1915), 2:318-320). Chlorinated oxidating agents exert strong microbicidal activity (Clark, P. A., et al., Infect. Immun. (1986), 53-2:252-256) and are so as to be only suitable for use in a simple in-vitro buffer system (Dakin, H. D., Br. Med. J. (1916), 1:852-854; Dakin, H. D., JAMA (1917), 69:27-30). Already in 1917 the use of synthetic chloramines was recommended for irrigation of wounds. Still now, it remains dubious, whether the final oxidizing agent is HOCl or the derivative chloramine. (Weiss, S. J., et al., Science (1983), 222:625-628). While hydrolising, lysozomal enzymes, derived from PMN degranulation, are considered a threat to various tissue-constituents, (Weiss, S. J., New Engl. J. Med. (1989), 320-6:365-376; Campbell, E. J., et al., J. Clin. Invest. (1982), 70:845-852) natural serum protease-inhibitors (alpha 1 protease inhibitor and alpha macroglubolin) are at large inactivated by its myeloperoxidase-oxydizing system. (Weiss, S. J., New Engl. J. Med. (1989), 320-6:365-376; Kramps, J. A., et al., Clin. Science (1988), 75:53-62) Bacterial derived toxins (low-molecular weight metabolic products, glycoproteins, lipopolysaccharides, proteases) are reported to initiate host tissue- and cell destruction as well as immune-cell activation. (Cimasoni, G., Monographs in Oral Science, Vol. 12.ed., H. M. Myers, Philadelphia, Pa., Karger (1983); Bom-vNoorloos et al., J. Clin. Periodontal. (1989), 16:412–418; Curtis, M. A., et al., J. Clin. Periodontal. (1989), 16:1–11; Carpenter, A. B., et al., Inf. Immun. (1984); 43-1:326–336). Some microorganisms are able to inactivate the human serum protease-inhibitors. (Carlsson, J., et al., Infect. Immun. (1984), 43-2:6-44-648; Morihara, M., et al., Infect. Immun. (1979); 24:188–193). Consequently, a potent inhibitor of elastase might prove to be a useful therapeutic tool to combat such diseases.

Studies have shown that the salivary glands of leeches contain a potent inhibitor to the enzyme elastase. In the leech species Hirudo medicinalis, apart from the thrombin inhibitor hirudin, an inhibitor to the enzymes chymotrypsin and elastase has also been observed. It has been named Eglin and has been purified and well characterized (Seemüller U., et al., Methyl Enzymol. (1981), 804–816). Goldstein et al, (Goldstein, A. M., et al., Comp. Biochem. Physiol. (1986); 84B:117-124) have reported the presence of Eglin in three different species of North American leeches. However, to our knowledge, the elastase-inhibitor from other species of leeches studied so far has similar biochemical properties.

In the present study, during the purification of anti-thrombin from a leech species Hirudinaria manillensis, we have isolated unintentionally, a novel inhibitor which has potent anti-chymotrypsin and anti-elastase activity. The results obtained so far indicate that this inhibitor is significantly different from Eglin, and has been named "Gelin".

Gelin was found during experiments for purification of proteins from leech species Hirudinaria manillensis. During the purification of these proteins, inhibitory activity towards chymotrypsin and elastase was observed in certain fractions, and these were studied for comparison with eglin and hirudin. The leech-derived elastase/chymotrypsin inhibitor, according to part of this invention (and corresponding DNA sequences, which can be extrapolated therefrom, or a corresponding synthetic polypeptide is non-homologous with Eglin, a known elastase/chymotrypsin inhibitor, of which it is known to be present in the medicinal leech Hirudo medicinalis and is described by: Seemüller et al.: Eglin: "elastase-catheps in G-inhibitor from leeches"; 1981: Meth.Enzymol.: 80:804-816.

Furthermore, comparisons with hirudin (Dodt et al.; FEBS 165,:180–184) and other known structures lead to the conclusion that the structure of Gelin is unique and very different from that of Eglin.

The elastase/chymotrypsin-inhibitor according to part of this invention is typically isolated from leech tissue by solvent extraction-techniques; alternatively it may be isolated from leech secretions; (such as leech saliva).

The other part of this invention relates to the novel use of Eglin in cosmetic preparations, such as, amongst others: mouth rinses, toothpastes, skin creams.

BRIEF DESCRIPTION OF THE DRAWINGS

FIG. 11A is the CD spectrum of gelin. FIG. 11B is the CD spectrum of eglin.

Purification 7 kg *Hirudinaria manillensis* were dehydrated in 96% ethanol at room temperature; four changes of 4,000 ml. The dehydrated bodies were removed and the ethanol extract representing the starting material was adjusted to pH 3.5 with concentrated HCl. The resulting solution was centrifuged at 1,000 rpm for 10 minutes and the pH of the supernatant readjusted to pH 7.0 with 0.1M NaOH. The supernatant was diluted to 50% with distilled water and then concentrated to 800 ml on a Millipore Pellicon Ultrafilter System using a 10,000 nominal molecular weight cut off filter.

Chromatography on CM-Sepharose

The concentrated product was applied to a CM Sepharose column, equilibrated with 50 mM sodium acetate pH 6.0. The eluate (material that did not bind to the column) was collected as one large fraction and assayed for anti-chymotrypsin and anti-elastase activity. The eluate which contained the active ingredient was concentrated to 400 ml by ultrafiltration using a 10,000 molecular weight cut off filter.

Chromatography on DEAE-Sepharose

The product was filtered and the filtrate applied to a DEAE-Sepharose Fats-Flow column pre-equilibrated with 20 mM Piperazine-HCl-buffer pH 5.5. The column was developed at a flow rate of 10 ml/min and the absorbance, pH and conductivity of the eluate recorded.

After washing, the bound material was eluted with a stepwise gradient of 0.1-0.4M NaCl in equilibration buffer and each of the eluting peaks was collected as a separate fraction for measurement of anti-chymotrypsin and anti-elastase activity. The active peak was desalted by dialysis overnight against distilled water.

Chromatography on O-Sepharose

The partially purified product was further purified by anion exchange chromatography on Q-Sepharose, pre-equilibrated with 20 mM Tris-HCl buffer, pH 7.5. The column was developed at a flow rate of 20 ml/min and the bound material was eluted with a linear gradient of 0-1M NaCl in equilibration buffer. The absorbance and the elastase inhibitory activity of the eluate was recorded. The active fraction was pooled and concentrated by ultrafiltration using a 10,000 molecular weight cut off filter.

Chromatography on Superdex 200

The concentrated material was gel filtered on a Superdex 200 column equilibrated in 50 mM Tris-HCl 0.1M NaCl buffer, pH 7.5. The active peak was pooled and lyophilized.

High Performance Liquid Chromatography

Figure 1:
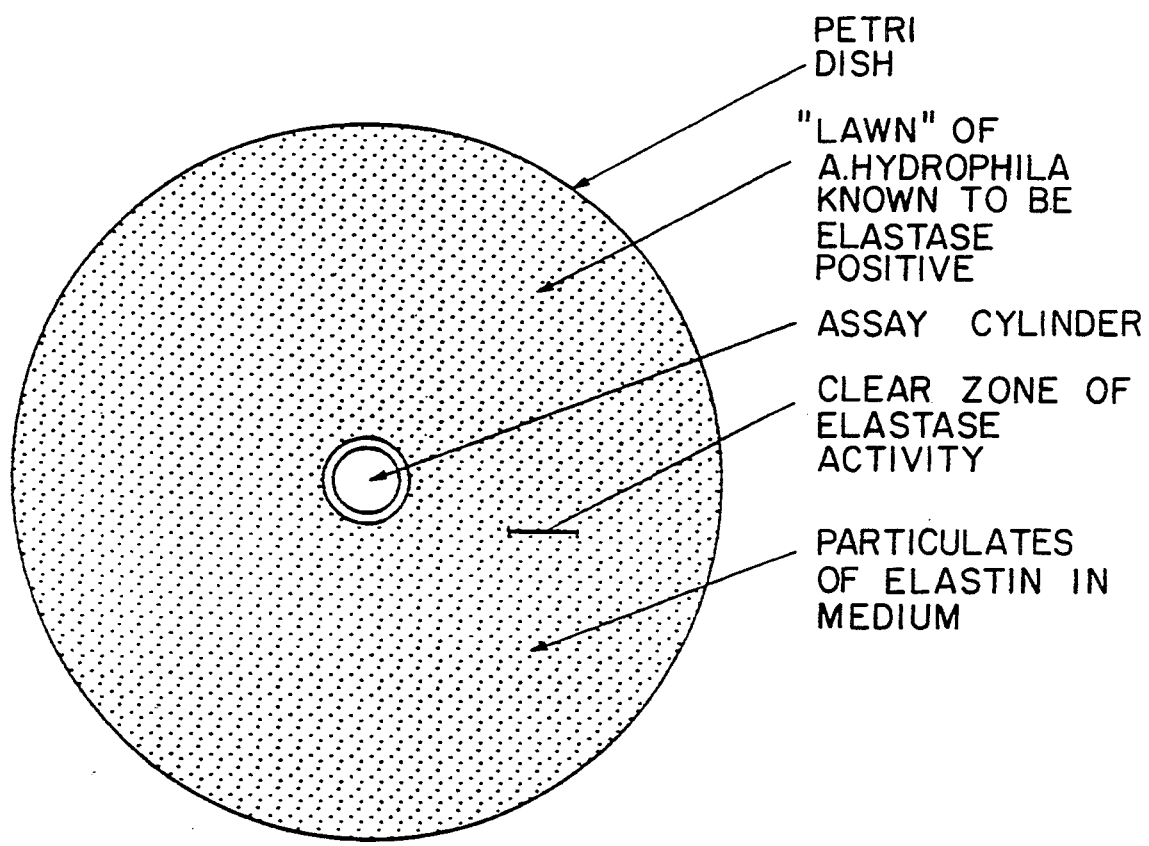
FIG. 1 is a diagram of the gelin activity assay.
Figure 2:
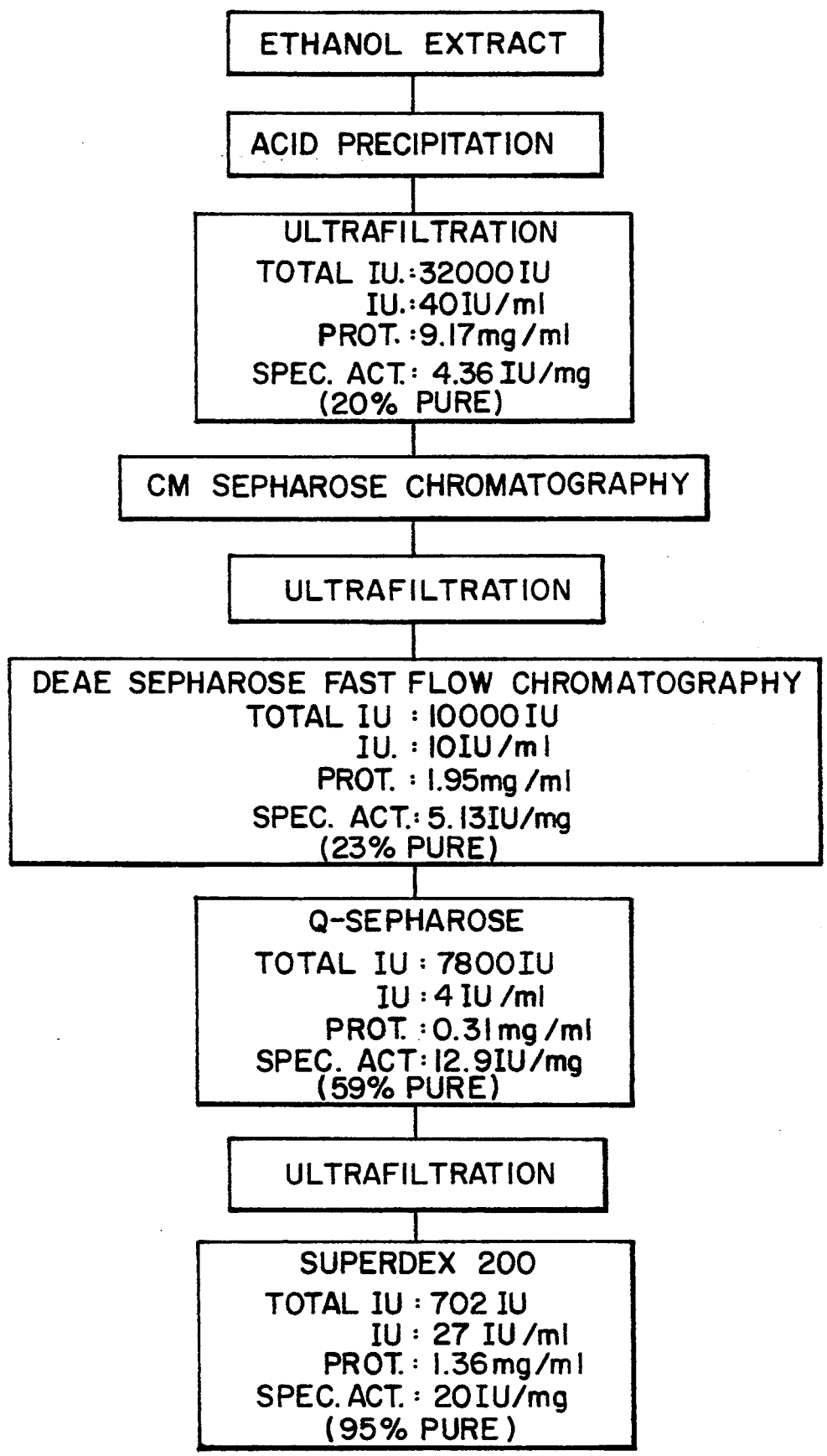
FIG. 2 is the purification schema for gelin.
Figure 3:
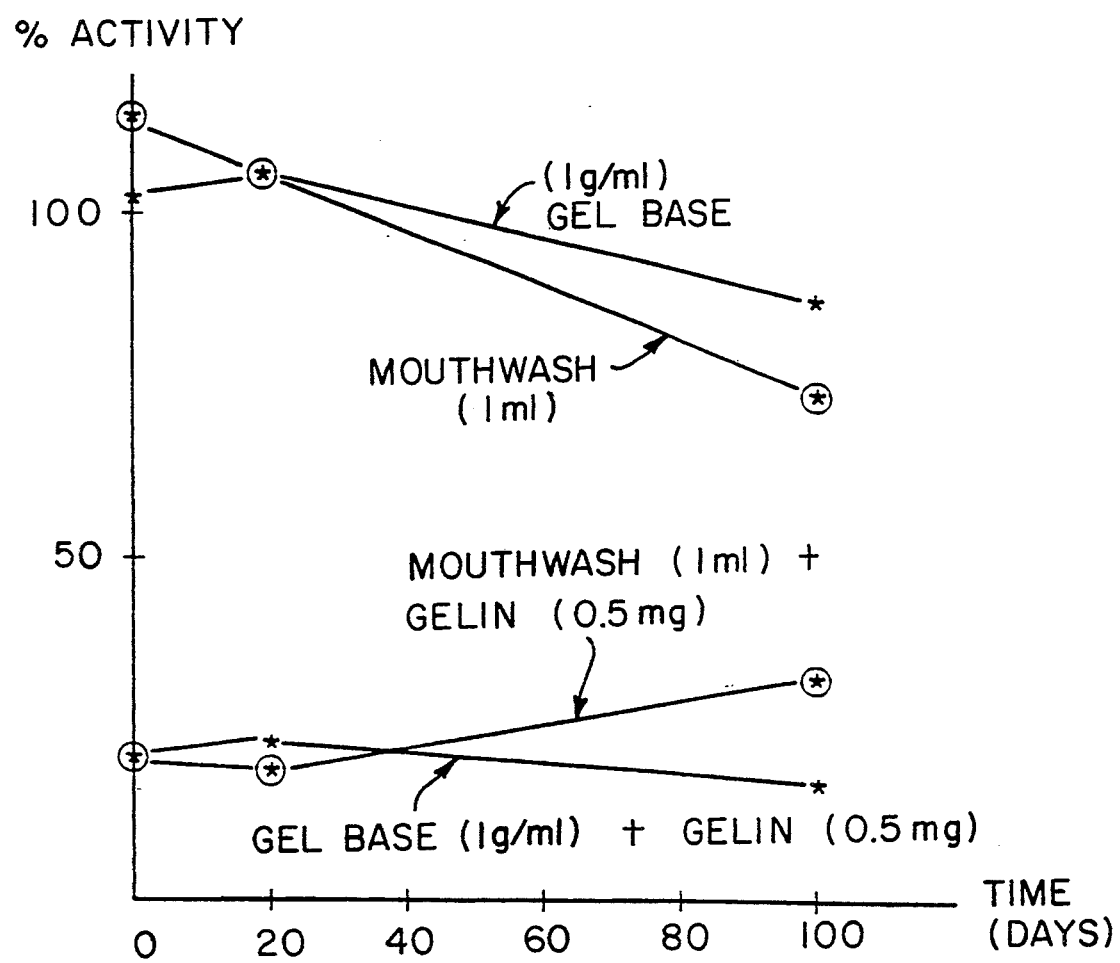
FIG. 3 graphically represents the long term stability of gelin over time, as reported in percent activity.
Figure 4:
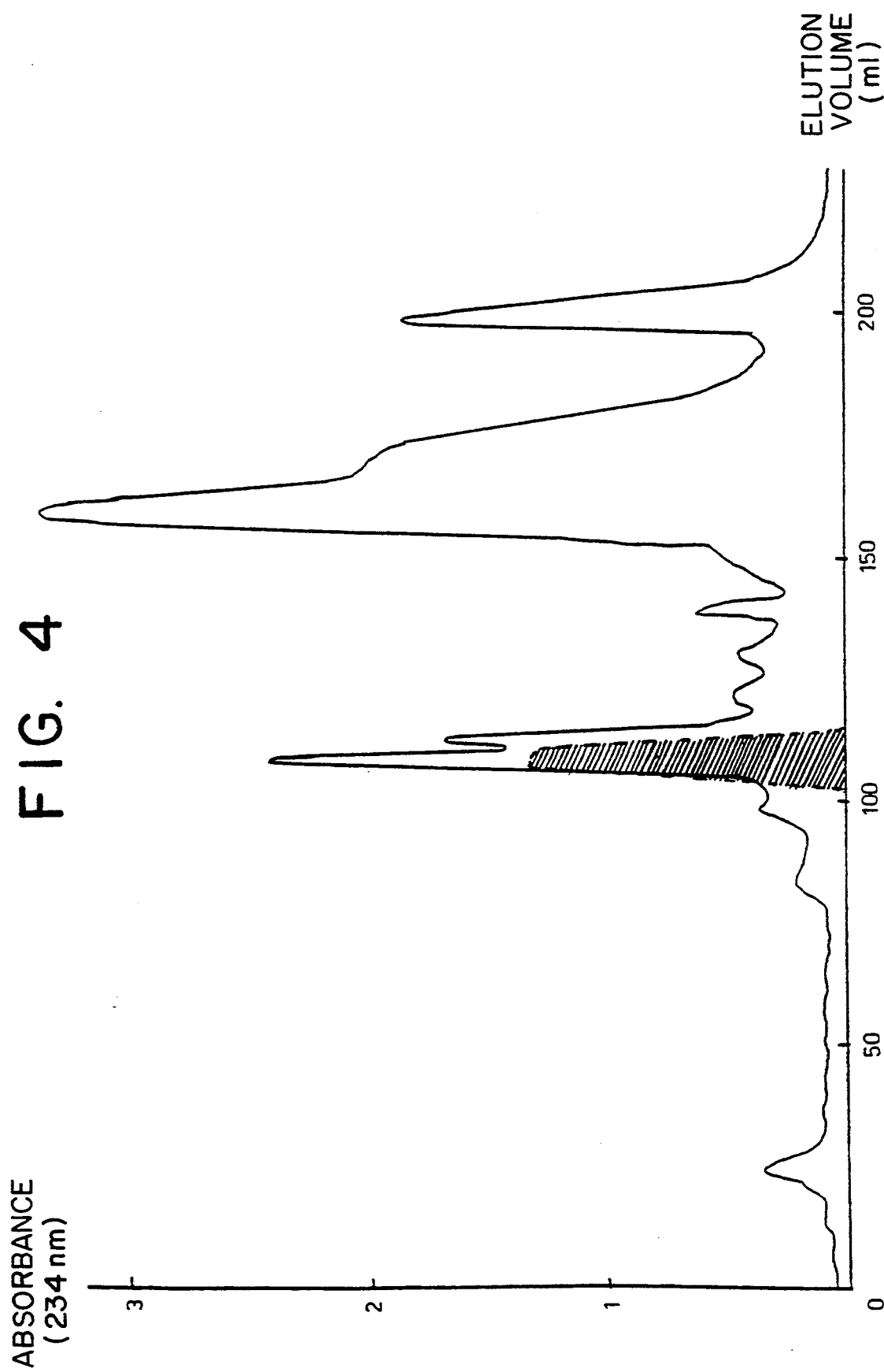
FIG. 4 is a chromatograph of gelin as eluted off DEAE-Sephadex.
Figure 5:
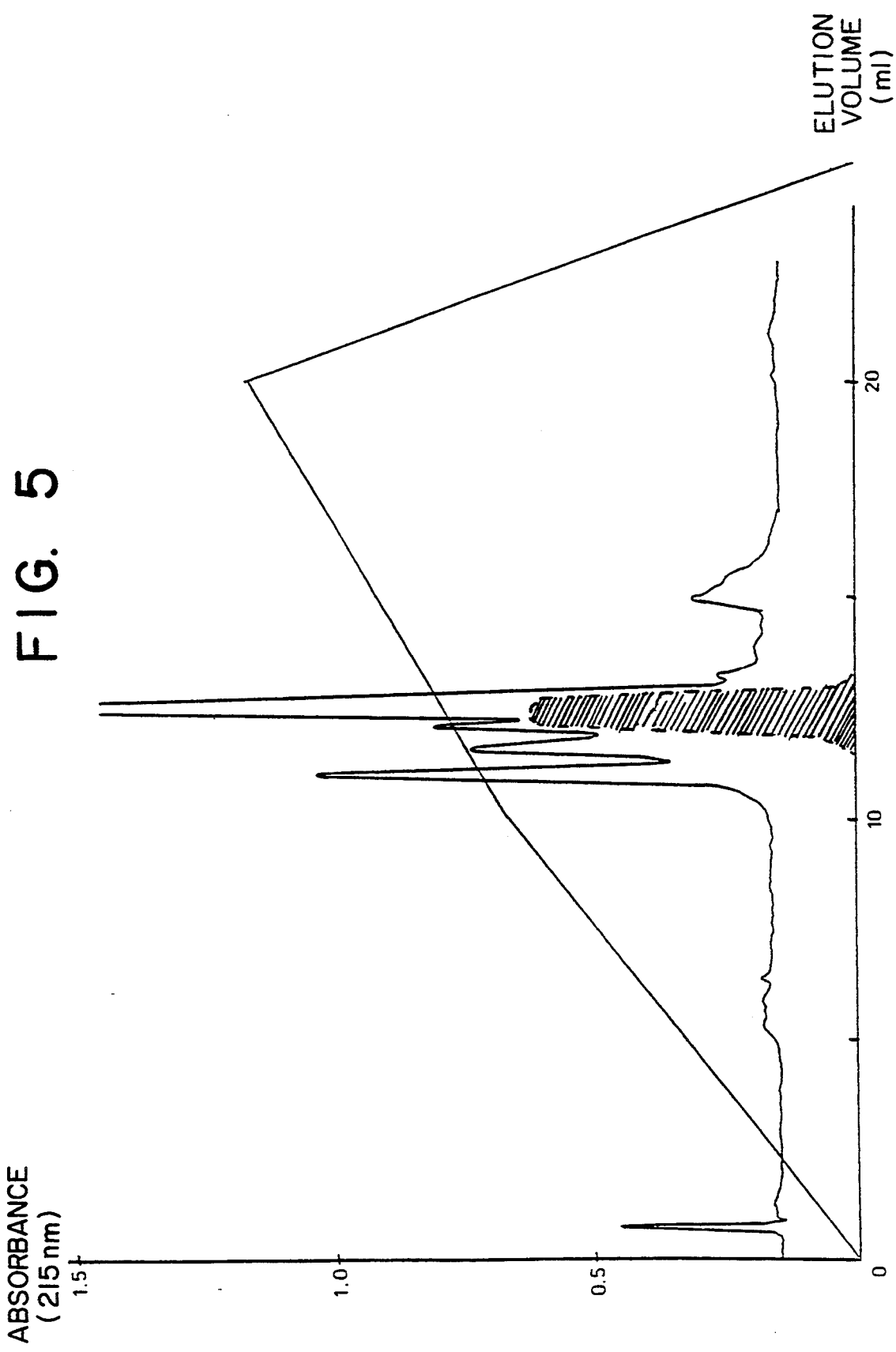
FIG. 5 is a chromatograph of gelin when purified using HPLC.

Partially purified sample was reconstituted and applied in aliquots to a reverse phase microbore Aquapore C8 column, equilibrated in 0,1% TFA. The bound material was eluted with 0-40% linear gradient of 60% $CH_3CN+0.09\%$ TFA over 10 minutes and 40-100% over 20 minutes. Each peak was collected as a separate fraction and checked for anti-elastase activity. (FIG. 5). The active peak was lyophilized and used for further studies.

The purity of the sample was assessed by repeat HPLC under similar conditions and by N-terminal sequence analysis. See scheme A for Gelin purification.

Biochemical studies

The elastase inhibitory activity of Gelin was measured spectrophotometrically by measuring the inhibition of the release of p-nitroaniline group from the synthetic substrate N-succinyl $(Ala)_3$-p-nitroanilide (SAAAP) catalyzed by pancreatic elastase. One inhibitory unit (IU) of activity is defined as the amount of Gelin necessary to inhibit the hydrolysis of 1 $\mu$ mole of SAAAP/min at pH 8.3 and 25° C.

The assay consists of incubating different amounts of Gelin with a known amount of pancreatic elastase in 0.1M Tris/HCl buffer, pH 8.3, containing 1M NaCl for 5 min at 25° C. The reaction is started by the addition of the chromogenic substrate and the absorbance at 405 nm monitored with time. A control reaction, in the absence of Gelin, is carried out under identical conditions. From absorbance change per min and using molar extinction coefficient of $10,5000 M^{-1}cm^{-1}$, the activity of Gelin can be calculated.

Protein estimation

Protein concentration of purified Gelin was estimated by Lowry and Bradford assays. It was found that there was a large discrepancy between the values obtained by these two methods. For a particular batch, 0.38 mg/ml was obtained by Lowry's method, but below the detection limit (<2 $\mu$g/ml) by Bradford assay. The value obtained by Lowry's method is, however, in close agreement with the value otained by absorbance at 280 nm, using E=10 for 1% solution. Using protein value estimated by Lowry's method, the specific activity of purified Gelin was found to be about 40-80 mIU/mg.

Isoelectric point

Figure 6:
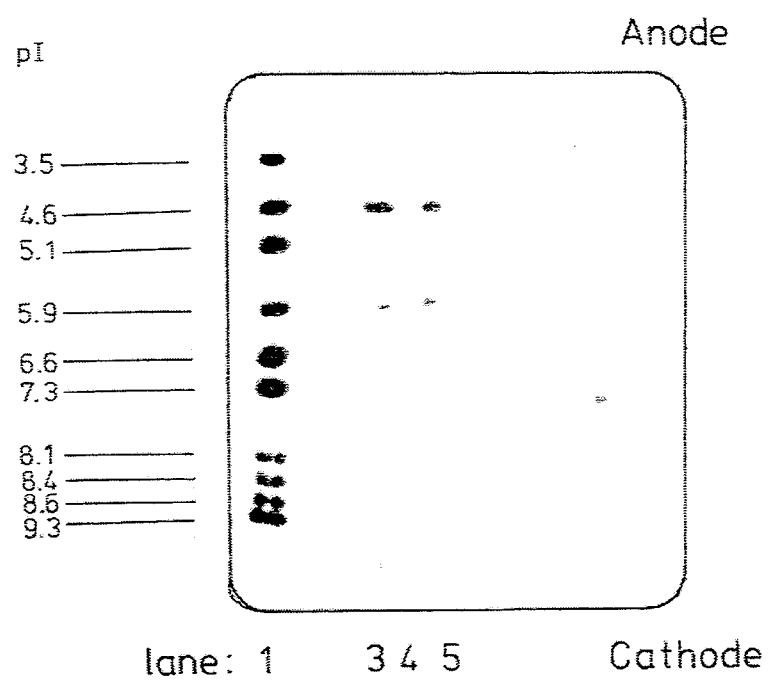
FIG. 6 is a gel of the isoelectric focusing of gelin. Lane 1=IEF markers, Lanes 3-5=gelin.

The pI of Gelin was determined using an isoelectric focusing gel of pH range 3 to 9, using a Pharmacia Phast system, according to manufacturer's instructions. Gelin was applied centrally on the gel. IEF markers used under identical conditions were amylglucosidase (3.5), trypsin inhibitor (4.6), B-lactoglobulin (5.1), carbonic anhydrase I and II (5.9 and 6.6), myoglobulin (6.7), lactic dehydrogenase (8.5) and trypsinogen (9.0). After focusing the gel was developed and the resulting bands were visualized by silver staining (FIG. 6).

The isoelectric point of Gelin was found to be about 4.6, as compared to the published report of 6.45 for Eglin C and 6.6 for Eglin B. (The two Eglins differ by one amino acid; histidine in Eglin B for tyrosine in Eglin C.).

Molecular weight

Figure 7A:
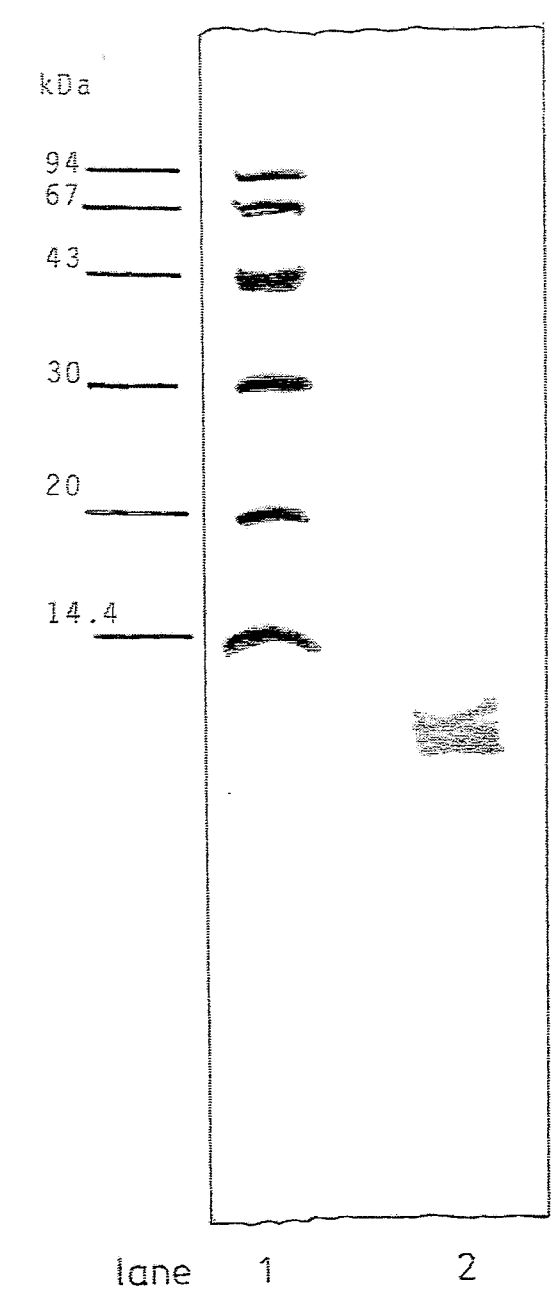
FIG. 7A is a SDS-PAGE using the Laemmli method, with Lane 1=molecular weight markers, range 14.4-94 kDa; Lane 2=gelin.
Figure 7B:
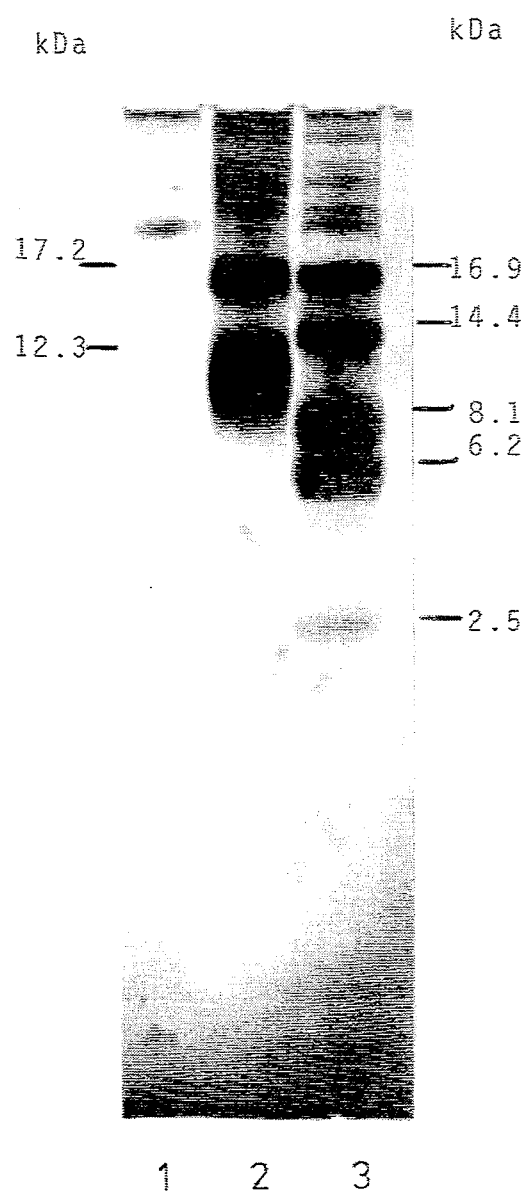
FIG. 7B is a SDS-PAGE using the Swank & Munkres method, with Lane 1=gelin; Lane 2=molecular weight markers, range 12.3-78 kDa; and Lane 3=molecular weight markers, range 2.3-16.9 kDa.

The molecular weight of Gelin was determined by SDS-polyacrylamide gel electrophoresis as described by Laemlli. (23). In both 16% and 20% homogeneous gel, purified Gelin migrated as a band just below 14.4 kDa under reducing conditions (FIG. 7A). Molecular weight markers used under identical conditions were phosphorylase B (94 kDa), bovine serum albumin (67 kDa), ovalbumin (43 kDa), carbonic anhydrase (30 kDa), trypsin inhibitor (20 kDa) and lactalbumin (14.4 kDa). However, when Gelin was analysed by SDS-PAGE in the presence of 8M urea, according to the method of Swank & Munkres (24), it was found that the sample was difficult to visualise when stained with Coomassie blue, but on silver staining, there was some indication that Gelin had a mobility which corresponded to a molecular weight of about 21–25 kDa. A low molecular weight "Electran" reference suitable for determination of molecular weight of small proteins and peptides by Swank & Munkres' method was used, as shown in FIG. 7B. This discrepancy in molecular weight by two different methods cannot be explained at present. (Eglin has a molecular weight of 8.1 kDa).

Specificity

The inhibitory activity of Gelin was compared against the following serine proteases: elastase, cathepsin G, chymotrypsin, trypsin and thrombin, using assay methods with chromogenic substrates. The details of the assay conditions used for each enzyme are outlined in Table 1. In brief, the fixed amount of enzyme is incubated with different concentrations of Gelin in the appropriate buffer at 37° C. for 5 min. The reaction is started by the addition of the substrate and the increase in absorbance is monitored at 405 nm. The initial rate of the control assay without the inhibitor was taken as 100% for each enzyme. From the data obtained the molar concentration of Gelin required to inhibit 50% of the enzyme activity ($IC^{50}$) was calculated. The results indicate that Gelin is a potent inhibitor towards chymotrypsin, cathepsin G and elastase, with little activity towards trypsin and thrombin. The $IC^{50}$ values calculated were 0.13, 0.25, 0.32, and 20.4 moles of Gelin/mole of chymotrypsin, cathepsin G, elastase and trypsin, respectively.

Amino acid composition

Purified gelin was hydrolysed with gaseous ARISTAR HCl under vacuum at 110° C. for 24 and 48 hrs. The hydrolysed mixture was analyzed for amino acid composition on an Amino Chrome system. For comparison with eglin c, a molecular weight of 8100 daltons was used for gelin for the quantification of the liberated amino acids. The results, as shown in Table 2, indicate that the composition is quite different for both the inhibitors. In particular, the presence of significant amounts of aspartic acid (+asparagine) and alanine, absence of histidine and the presence of isoleucine in gelin, compared to eglin c.

Circular Dichroism

CD spectrum of anti-elastase was obtained using 0.02 cm pathlength cell in 0.1% TFA at room temperature. This spectrum was compared with that obtained with rec-eglin (FIGS. 11A and 11B), the latter was a gift from Ciba Geigy, Basel. The data, when evaluated by CONTIN analysis, indicate that the tertiary structure of gelin has no helix, 58% beta sheets and 42% non-ordered structures, compared to 19% helix, 56% beta sheets and 25% non-ordered structures in eglin c. Thus the elastase inhibitor from two different species of leeches are markedly different and further supports the differences observed in their N-terminal amino acid sequences (see below).

Structural studies

N-terminal amino acid sequence of purified anti-elastase was determined and this resulted in a single sequence upto residue 29. In order to confirm the presence of cysteine residues in the sequence, purified sample was reduced with dithiothreiotol and the cysteine derivatized to pyridytethyl cysteine by reaction with 4-vinyl pyridine. Amino terminal sequence analysis of this derivatized sample was repeated and the results obtained are shown in Table 3. Comparison of this partial sequence with the published data of eglin shows that this inhibitor is markedly different in its primary structure.

In order to determine the complete primary sequence of gelin, purified material was reduced, and derivatized as before, and then digested with either TPCK-trypsin, TLCK-chymotrypsin or V8 protease, under following conditions.

Figure 8:
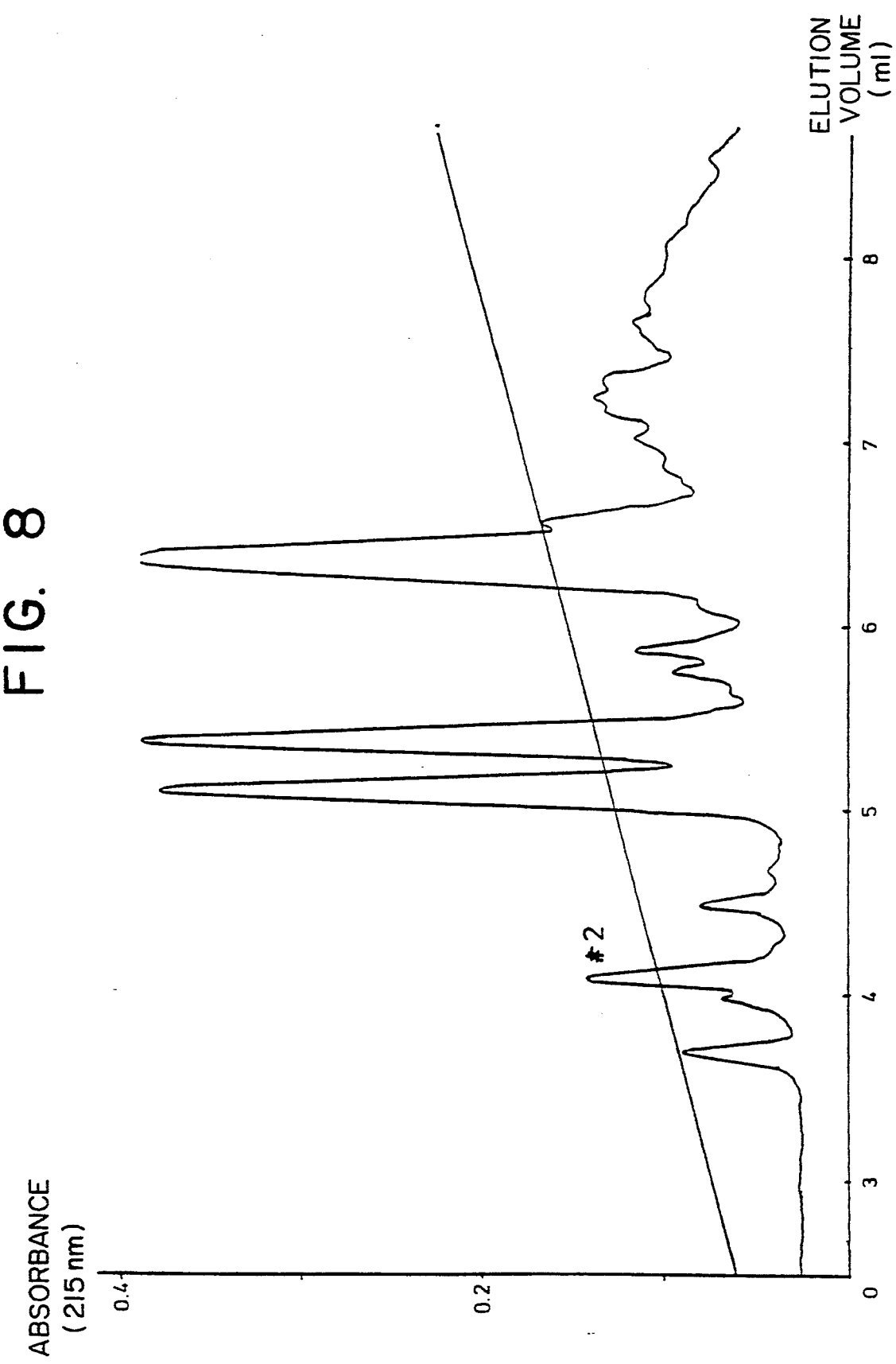
FIG. 8 is a chromatograph of the separation of a tryptic digest of gelin.

Gelin was digested with TPCK treated trypsin in the ratio 50:1 (wt/wt) of gelin to trypsin. The reaction was carried out in 0.1 ml of 0.05M ammonium bicarbonate buffer, pH 8.0 at 37° C. for 4 hrs. The reaction was terminated by freeze drying and the tryptic peptides separated by HPLC. (FIG. 8).

Figure 9:
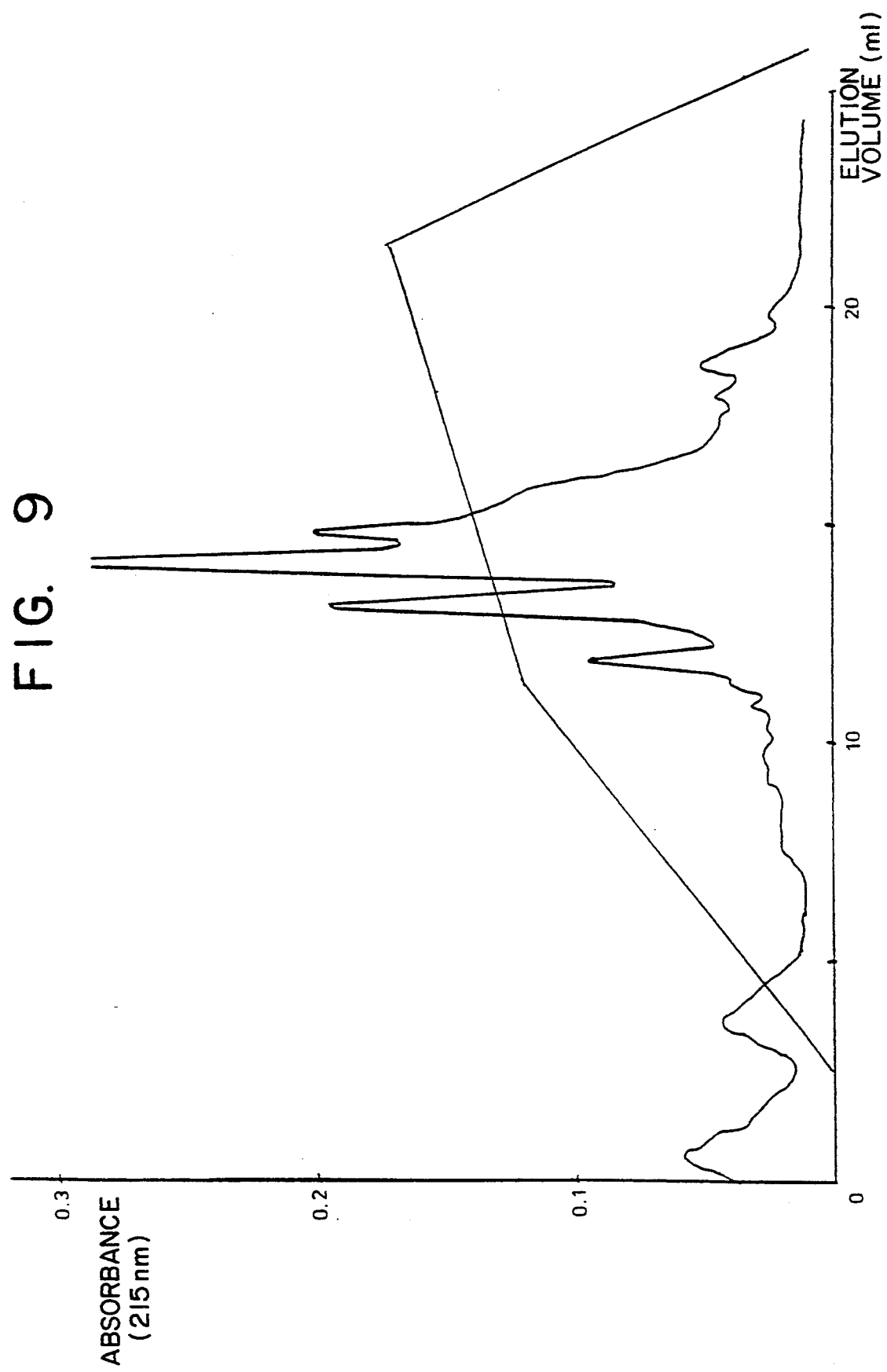
FIG. 9 is a chromatograph of the separation of a chymotryptic digest of gelin.
Figure 10:
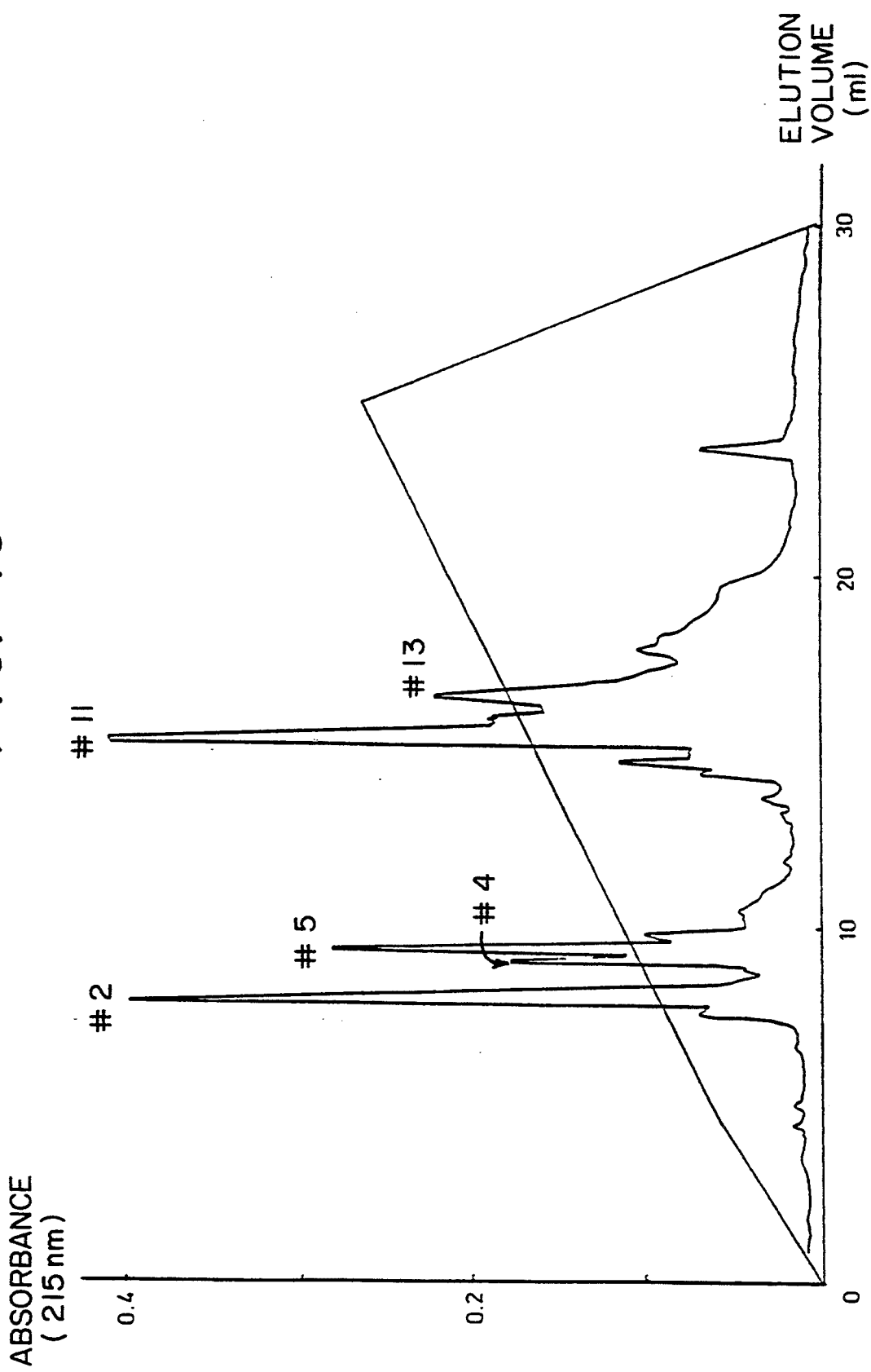
FIG. 10 is a chromatograph of the separation of a *Staph. aureus* V8 digest of gelin.

Digestion with TLCK-treated chymotrypsin was carried out under similar conditions as described above. The generated peptide fragments were separated by HPLC (FIG. 9). For digestion with protease V8, purified gelin was mixed with 5 μg of enzyme in 0.05M ammonium bicarbonate buffer, pH 7.9. The mixture was incubated at room temperature for 24 hrs before separation of the generated fragments by HPLC (FIG. 10).

Solubility and stability

Equal aliquots of gelin were dehydrated under vacuum over silica gel. Each aliquot was then dissolved in either acetic acid, ethanol, butanol, acetone, (all Analar grade reagents) or distilled water and stirred for 10 min at room temperature. The solvent from each sample was then decanted into fresh vials and lyophilised. The total amount of gelin, in terms of inhibitory units (IU), was determined by chromogenic assay.

Results obtained indicate that gelin is stable in all the solvents tested under the above conditions, with the order of solubility being water>acetic acid>ethanol>acetone>butanol.

Temperature stability

In a separate experiment, it was found that Gelin is stable at higher temperatures, at 100° C. for up to 30 min with negligible loss of inhibitory activity.

| STANDARD OPERATING PROCEDURE GELIN ASSAY | CODE GEL 1 | PAGE 1 |
| --- | --- | --- |

PRINCIPLE OF ASSAY

Gelin is a novel protease inhibitor derived from the leech. The basis of the assay involves the inhibition of α-chymotrypsin activity on the synthetic chromogenic substrate S-2586. α-Chymotrypsin activity can be measured spectrophotometrically (at 405 nm) by monitoring the release of a coloured p-nitroaniline group liberated during substrate digestion. The reduction in α-chymotrypsin activity in the presence of gelin is related to the inhibitory activity.

UNIT DEFINITION

One unit of α-chymotrypsin activity (U) will hydrolyse 1 umole of S-2586/min at pH8.3, 25° C. One unit of inhibitory activity (IU) will reduce the enzyme catalysed hydrolysis by 1 umole of S-2586/min at pH8.3, 25° C.

| STANDARD OPERATING PROCEDURE GELIN ASSAY | CODE GEL 1 | PAGE 2 |
|---|---|---|

MATERIALS

| Chemicals | Supplier | |
|---|---|---|
| α-Chymotrypsin | Sigma | C2419 |
| S-2586 | Kabi Vitrum | 820894 |
| Acetic Acid - Glacial | BDH | 10001 |
| NaCl | Sigma | S9625 |
| Tris | Sigma | T1503 |
| HCl | BDH | 10307 |
| Gelin | In house preparation | |

Apparatus
96 'U' well Microtitre plate — Midland Laboratories
Titertek Uniskan II Microtritre Plate Reader (equipped with 405 nm light filter) — Flow Laboratories

| STANDARD OPERATING PROCEDURE GELIN ASSAY | CODE GEL 1 | PAGE 3 |
|---|---|---|

SOLUTION PREPARATION

1. Assay Buffer
   0.1M Tris/HCl pH 8.3, 1M NaCl
2. Chymotrypsin Solution
   4 ug/ml α-Chymotrypsin in H$_2$O
3. Chromogenic Substrate
   1. OmM S-2586 in H$_2$O
4. 50% Glacial Acetic Acid
   Glacial Acetic Acid diluted 1:1 in H$_2$O

| STANDARD OPERATING PROCEDURE GELIN ASSAY | CODE GEL 1 | PAGE 4 |
|---|---|---|

ASSAY PROCEDURE

1. The assay is performed in wells of a microtitre plate. Each well contains:
   100 ul Assay buffer
   50 ul Sample protease inhibitor
   50 ul Chymotrypsin solution
2. The contents are incubated at 25° C. for 5 mins.
3. The reaction is started by the addition of (25 ul) chromogenic substrate solution (S-2856 1 mM). The starting time (t) is noted and the reaction mixture incubated at 25° C. for 5 min. Under these conditions the substrate concentration is not limiting.
4. The reaction is stopped by the addition of 25 ul 50% Acetic Acid.
5. The absorbance of released p-nitroaniline is read at 405 nm on a microplate reader.

NOTE

For samples which have an intrinsic absorbance at 405 nm blanks must be run to remove absorbance changes by the sample alone. The blank should be run under parallel assay conditions but without the addition of S-2586.

To standardize the assay procedure an in house gelin control of known inhibitory activity should be run under identical conditions to the test sample.

| STANDARD OPERATING PROCEDURE GELIN ASSAY | CODE GEL 1 | PAGE 5 |
|---|---|---|

DETERMINATION OF INHIBITORY ACTIVITY

1. Inhibitory activity of the test sample is determined by direct comparison with the inhibitory activity of a known in house gelin standard. Quantification of activity is determined by computer assisted dose ratio analysis of dilution curves from the test sample and standard material.
2. Alternatively the inhibitory activity of the test sample can be calculated by using the equation.

$A = Ecl$ where
   $A$ = Absorbance
   $E$ = Molar extinction coefficient ($M^{-1}cm^{-1}$)
   $c$ = Concentration of product (M)
   $l$ = Path length (cm)

The molar extinction coefficient for the coloured product may be determined experimentally by incubating a known quantity of substrate with α-chymotrypsin until the reaction is complete (i.e. no further colour change).

This value of E had been determined to be 10,500 $M^{-1}cm^{-1}$ for an absorbance at 405 nm.

The difference in concentration of product produced per minute under inhibitory and non inhibitory conditions determines the inhibitory activity of the test sample.

| STANDARD OPERATING PROCEDURE GELIN ASSAY | CODE GEL 2 | PAGE 1 |
|---|---|---|

PRINCIPLE OF ASSAY

Gelin is a novel protease inhibitor derived from the leech. The basis of the assay involves the inhibition of elastase activity on the synthetic chromogenic substrate SAAAP. Elastase activity can be measured spectrophotometrically (at 405 nm) by monitoring the release of a coloured p-nitroaniline group liberated during substrate digestion. The reduction in elastase activity in the presence of gelin is related to the inhibitory activity.

UNIT DEFINITION

One unit of elastase activity (U) will hydrolyse 1 umole of SAAAP/min at pH 8.3, 25° C. One unit of inhibitory activity (IU) will reduce the enzyme catalysed hydrolysis by 1 umole of SAAAP/min at pH8.3, 25° C.

| STANDARD OPERATING PROCEDURE GELIN ASSAY | CODE GEL 2 | PAGE 2 |
|---|---|---|

MATERIALS

| Chemicals | Supplier |
|---|---|

| | | |
|---|---|---|
| Elastase | Sigma | E1250 |
| SAAAP: N-Succinyl-L(-Alanine)3-p-Nitroanilide | Calbiochem | 573459 |
| Acetic Acid - Glacial | BDH | 10001 |
| NaCl | Sigma | S9625 |
| Tris | Sigma | T1503 |
| HCl | BDH | 10307 |
| Gelin | In house preparation | |
| Apparatus | | |
| 96 'U' well microtitre plate | Midland Laboratories | |
| Titertek Uniskan II Microtritre Plate Reader (equipped with 405 nm light filter) | Flow Laboratories | |

| STANDARD OPERATING PROCEDURE | CODE | PAGE |
|---|---|---|
| GELIN ASSAY | GEL 2 | 3 |

SOLUTION PREPARATION

1. Assay Buffer
   0.1M Tris/HCl pH 8.3, 1M NaCl
2. Elastase Solution
   40 ug/ml Elastase in H$_2$O
3. Chromogenic Substrate
   1.0mM SAAAP in H$_2$O
4. 50% Glacial Acetic Acid
   Glacial Acetic Acid diluted 1:1 in H$_2$O

| STANDARD OPERATING PROCEDURE | CODE | PAGE |
|---|---|---|
| GELIN ASSAY | GEL 2 | 4 |

ASSAY PROCEDURE

1. The assay is performed in wells of a microtitre plate.

Each well contains:
   100 ul Assay buffer
   50 ul Sample protease inhibitor
   50 ul Elastase solution 2. The contents are incubated at 25° C. for 5 mins.
3. The reaction is started by the addition of (25 ul) chromogenic substrate solution (SAAAP 1 mM). The starting time (t) is noted and the reaction mixture incubated at 25° C. for 30 min. Under these conditions the substrate concentration is not limiting.
4. The reaction is stopped by the addition of 25 ul 50% Acetic Acid.
5. The absorbance of released p-nitroaniline is read at 405 nm on a microplate reader.

NOTE

For samples which have an intrinsic absorbance at 405 nm blanks must be run to remove absorbance changes by the sample alone. The blank should be run under parallel assay conditions but without the addition of SAAAP.

To standardize the assay procedure an in house gelin control of known inhibitory activity should be run under identical conditions to the test sample.

| STANDARD OPERATING PROCEDURE | CODE | PAGE |
|---|---|---|
| GELIN ASSAY | GEL 2 | 5 |

DETERMINATION OF INHIBITORY ACTIVITY

1. Inhibitory activity of the test sample is determined by direct comparison with the inhibitory activity of a known in house gelin standard. Quantification of activity is determined by computer assisted dose ratio analysis of dilution curves from the test sample and standard material.
2. Alternatively the inhibitory activity of the test sample can be calculated by using the equation.

A=Ecl where
   A=Absorbance
   E=Molar extinction coefficient $(M^{-1}cm^{-1})$
   c=Concentration of product (M)
   l=Path length (cm)

The molar extinction coefficient for the coloured product may be determined experimentally by incubating a known quantity of substrate with Elastase until the reaction is complete (i.e. no further colour change).

This value of E had been determined to be $10,500 M^{-1}cm^{-1}$ for an absorbance at 405 nm.

The difference in concentration of product produced per minute under inhibitory and non inhibitory conditions determines the inhibitory activity of the test sample.

| STANDARD OPERATING PROCEDURE | CODE | PAGE |
|---|---|---|
| GELIN ASSAY | GEL 3 | 1 |

PRINCIPLE OF ASSAY

Gelin is a novel protease inhibitor derived from the leech. The basis of the assay involves the inhibition of trypsin activity on the synthetic chromogenic substrate S-2238. Trypsin activity can be measured spectrophotometrically (at 405 nm) by monitoring the release of a coloured p-nitroaniline group liberated during substrate digestion. The reduction in trypsin activity in the presence of gelin is related to the inhibitory activity.

UNIT DEFINITION

One unit of trypsin activity (U) will hydrolyse 1 umole of S-2238/min at pH8.3, 25° C. One unit of inhibitory activity (IU) will reduce the enzyme catalysed hydrolysis by 1 umole of S-2238/min at pH8.3, 25° C.

| STANDARD OPERATING PROCEDURE | CODE | PAGE |
|---|---|---|
| GELIN ASSAY | GEL 3 | 2 |
| MATERIALS | | |
| | | Supplier |
| Chemicals | | |
| Trypsin | Sigma | T8253 |
| S-2238 | Kabi Vitrum | 820324 |
| Acetic Acid - Glacial | BDH | 10001 |
| NaCl | Sigma | S9625 |
| Tris | Sigma | T1503 |
| HCl | BDH | 10307 |
| Gelin | In house preparation | |
| Apparatus | | |

-continued

| 96 'U' well Microtitre plate | Midland Laboratories |
|---|---|
| Titertek Uniskan II Microtitre Plate Reader (equipped with 405 nm light filter) | Flow Laboratories |

| STANDARD OPERATING PROCEDURE | CODE GEL 3 | PAGE 3 |
|---|---|---|
| GELIN ASSAY | | |

SOLUTION PREPARATION

1. Assay Buffer
   0.1M Tris/HCl pH 8.3, 1M NaCl
2. Elastase Solution
   40 ug/ml Trypsin in $H_2O$
3. Chromogenic Substrate
   1.0mM S-2238 in $H_2O$
4. 50% Glacial Acetic Acid
   Glacial Acetic Acid diluted 1:1 in $H_2O$

| STANDARD OPERATING PROCEDURE | CODE GEL 3 | PAGE 4 |
|---|---|---|
| GELIN ASSAY | | |

ASSAY PROCEDURE

1. The assay is performed in wells of a microtitre plate.

Each well contains:
   100 ul Assay buffer
   50 ul Sample protease inhibitor
   50 ul Trypsin solution 2. The contents are incubated at 25° C. for 5 mins.
3. The reaction is started by the addition of (25 ul) chromogenic substrate solution (S-2238 1 mM). The starting time (t) is noted and the reaction mixture incubated at 25° C. for 5 min. Under these conditions the substrate concentration is not limiting.
4. The reaction is stopped by the addition of 25 ul 50% Acetic Acid.
5. The absorbance of released p-nitroaniline is read at 405 nm on a microplate reader.

NOTE

For samples which have an intrinsic absorbance at 405 nm blanks must be run to remove absorbance changes by the sample alone. The blank should be run under parallel assay conditions but without the addition of S-2238.

To standardize the assay procedure an in house gelin control of known inhibitory activity should be run under identical conditions to the test sample.

| STANDARD OPERATING PROCEDURE | CODE GEL 3 | PAGE 5 |
|---|---|---|
| GELIN ASSAY | | |

DETERMINATION OF INHIBITORY ACTIVITY

1. Inhibitory activity of the test sample is determined by direct comparison with the inhibitory activity of a known in house gelin standard. Quantification of activity is determined by computer assisted dose ratio analysis of dilution curves from the test sample and standard material.
2. Alternatively the inhibitory activity of the test sample can be calculated by using the equation.

$A = Ecl$ where
   $A$ = Absorbance
   $E$ = Molar extinction coefficient ($M^{-1}cm^{-1}$)
   $c$ = Concentration of product (M)
   $l$ = Path length (cm)

The molar extinction coefficient for the coloured produce may be determined experimentally by incubating a known quantity of substrate with trypsin until the reaction is complete (i.e. no further colour change).

This value of E had been determined to be $10,500 M^{-1}cm^{-1}$ for an absorbance at 405 nm.

The difference in concentration of product produced per minute under inhibitory and non inhibitory conditions determines the inhibitory activity of the test sample.

PRELIMINARY PILOT STUDY ON GINGIVITIS

A number of 8 volunteers were selected for this study. Criteria for selection were: visible plaque accumulation, chronic gingivitis on at least 4 teeth with sulcular pocket depths, between 3 and 5 mm, bleeding on probing, absence of open caries and severe periodontitis, in general good health otherwise, no record of recent medication. Subjects were males and females in the age range 23 to 46 years.

The experiment consisted of a daily subgingival irrigation on 4 teeth during 6 days executed by a general practitioner. Measurements were taken at baseline and at day 6. Subjects were instructed not to alter their usual oral hygiene procedures. Measurements taken were: PI (Plaque Index, according to Silness and Loe, Acta. Odont. Scand. 1964; 22:121) and PBI (Papillary Bleeding Index according to Muhlemann, H. R.: J. Prev. Dent. 1977; 4:6). All subjects followed the same treatment, there was no negative control. 6 received the test material, 2 received a placebo. Lyophilized dry-powder Gelin was solubilized as 20 mg Gelin to 8 ml of a standard solution. This standard solution consisted of a sterile mixture of isotonic water/glycerol (60%/40%) with 2% b.w. of sodium carboxy-methyl cellulose added and stirred until gelled.

This gel was then divided for each subject in sterile micro-injecting-syringes with hollow needles.

Each subgingival irrigation consisted of injecting 0.05 ml of the standard gel solution containing the Gelin into each periodontal pocket around the designated teeth.

Results

At baseline the $\bar{x}$ PI for the test group was: $2.2 \pm 0.7$.
At baseline the $\bar{x}$ PBI for the test group was: $2.3 \pm 0.8$.
At the end of the experiments x PI was reduced to $1.0 \pm 0.6$, while x PBI was reduced to $0.6 \pm 0.3$.
The baseline data for the placebo subjects was $\bar{x}$ PBI $= 2.0 \pm 0.6$ and $\bar{x}$ PBI $= 2.4 \pm 1.0$.
At the end of the experiment the $\bar{x}$ PI for the placebo was reduced to $1.7 \pm 0.7$ and the $\bar{x}$ PBI was then $1.9 \pm 0.6$.

The reduction in PI for the test group was 55% compared to baseline and 42% compared to placebo.

The reduction in PBI for the test group was 74% compared to baseline and 65% compared to placebo.

Discussion

The important clinical very significant reduction in PBI as tested points towards the protease-inhibiting mechanism, which inhibits PMN-derived neutral proteases (elastase, cath G.) to proteolize gingival substrates. The less important, but significant reduction in plaque accumulation is surprising, although welcome. This effect is probably due to the fact that the inhibition of proteolysis of supporting tissues reduces the quantity of nutrients necessary for the viability of periodontopathic micro-organisms in dental plaque.

Effects on Plasmin

Experiments were performed to determine the inhibiting activity of Gelin on Plasmin. Plasmin activity was recorded by measuring the digestion and release of p-nitroanilide from the chromogenic substrate S-2288 (H-DlIle-Pro-Arg-pNA). Plasmin (50 μl, 40 μg/ml) was incubated with Gelin of varying concentrations (50 μl, 10 μg/ml, 5 μg/ml, 2.5 μg/ml and 1.25 μg/ml). Results indicate that even at the highest Gelin concentration (10 μg/ml) no inhibition of plasmin occurs.

Effects on Pepsin

Experiments were performed to determine the inhibitory activity of Gelin on the acidic protease Pepsin. Pepsin activity was recorded by measuring the proteolysis of haemoglobin at pH 2.0. Pepsin (25 μl, 8 mg/ml in dH$_2$O) was incubated with haemoglobin substrate (100 μl, 10 mg/ml in 20% acetic acid, pH 2.0) for 60 minutes at 37° C. in the presence and absence of Gelin inhibitor. Undigested haemoglobin was precipitated using trichloroacetic acid (100 μl, 10% w/v) and the hydrolysed protein in the supernatant measured at 280 nm. Results indicate that even at high concentrations of Gelin (75 μg/ml) there is no inhibitory effect on Pepsin. In addition, preliminary experiments suggest that Gelin was not cleaved by Pepsin.

Secretory origin of Gelin (1)

*Hirudinaria manillensis* leeches were carefully dissected into three portions: head, body and gut lining. Each component was well washed with distilled water to remove contaminants (e.g. blood). Each portion was dehydrated in ethanol and the extract assayed for inhibition of elastase.

Most of the activity (>75%) was located in the body extract.

Secretory origin of Gelin (2)

Individual leeches were made to secrete mucus by immersing in 8% ethanol. The mucus was collected and extracted five times with distilled water. The extracts were combined and assayed for inhibitory activity using the standard protocol.

Preliminary results indicate that inhibitory activity is present in the mucus extract. The total Gelin activity present in the mucus secretion is less than that determined for the ethanol extract harvested in the scheme for the partial purification of Gelin.

Long term incubation

Aliquots of Gelin were incubated in a variety of toothpaste gel bases as well as a mouthwash to determine the stability at room temperature over long periods. (i.e. shelf life).

Temperature fluctuations of between 17° C.–36° C. were recorded over the 100-day period.

Gelin retained its inhibiting activity against chymotryosin in all gel bases tested as well as in the mouthwash. Scheme B shows a typical time-course profile for a gel base and mouthwash in the presence and absence of 0.5 g Gelin (50 μl of 10 μg/ml).

Stability to oxidation

Two experiments were performed to determine the stability of Gelin to oxidation.

EXPERIMENT 1

Gelin (50 μl, 10 μg/ml in dH$_2$O) was incubated with hydrogen peroxide (30%, 50 μl in dH$_2$O) and lactoperoxidase (50 μl, 1 μg/ml in 50 μM Na Acetate, pH 6.0) for 1 hr. at 37° C. An aliquot (50 μl) was removed and assayed for inhibitory activity versus chymotrypsin.

The results are in the following table.

| | Results: | | | | | | | |
|---|---|---|---|---|---|---|---|---|
| | 1 | 2 | 3 | 4 | 5 | 6 | 7 | 8 |
| 50 l Gelin | + | + | − | + | − | − | + | − |
| 50 l L.peroxid. | + | − | − | − | − | + | + | + |
| 50 l 30% H$_2$O$_2$ | + | + | − | − | + | − | − | + |
| Abs. 405 (n = 3) | .063 | .061 | .658 | .056 | .596 | .614 | .067 | .622 |
| (±SD) | .005 | .002 | .002 | .005 | .013 | .012 | .004 | .005 |

CONCLUSION

Under the above conditions Gelin is stable to oxidation and retains its inhibiting activity.

EXPERIMENT 2

Gelin or Eglin (50 μl, 10 μg/ml in dH$_2$O) was incubated with hydrogen peroxide (30%, 50 μl in dH$_2$O) for 5 min. at 37° C. An aliquot (50 μl) was removed and assayed for inhibitory activity versus chymotrypsin.

The results are in the following table.

| | Results: | | | | | | | | |
|---|---|---|---|---|---|---|---|---|---|
| | 1 | 2 | 3 | 4 | 5 | 6 | 7 | 8 | 9 |
| 50 l Gelin | + | + | − | − | | | | | − |
| 50 l Eglin | | | | | + | + | − | − | − |
| 50 l H$_2$O$_2$ | + | − | + | − | + | − | + | − | + |
| Abs. 405 (n = 3) | .085 | .060 | .640 | .656 | .060 | .059 | .563 | .611 | .055 |
| (±SD) | .006 | .001 | .019 | .007 | .003 | .002 | .031 | .010 | .057 |

CONCLUSION

Under the conditions described the inhibitory action of Eglin is unaffected. For Gelin the inhibitin action appears to be minimally effected; (Compare tubes 1 and 2), and corresponds to 8%.

Preliminary experiment on antibacterial activity

Isolates of *Aeromonas hydrophila* were recovered from engorged leeches. Subsequent identification of the protease profile showed them to be elastase positive utilizing an assay described by Shotts et al. (Extracellular proteolytic activity of *Aeromonas hydrophila* complex. Fish Pathology (1985), 20:37–44). A vial of Gelin containing 1 mg was reconstituted in 1 ml and subsequent dilutions made from $10^{-1}$–$10^{-6}$. A selected culture of *A.hydrophila* was inoculated on the previously described assay medium so as to achieve a "lawn". A "penicillin" assay cylinder was placed at the center of the plates. One-tenth ml (0.1 ml) of the diluted Gelin was introduced into the respective cylinder and the plates were incubated for 10 days at 25° C. Findings indicated a blockage of elastase activity within the diffusion zone of the Gelin with a slight zone of elastase activity beyond. This was noted to occur at undiluted, $10^{-1}$, $10^{-2}$, and $10^{-3}$.

At the above dilutions of $10^{-1}$, $10^{-2}$ and $10^{-3}$ antielastase inhibitory units (IU) are calculated to be respectively 2 IU, 0.2 IU and 0.02 IU.

See diagram of Gelin activity.

Examples of preparations

The following toothpastes with the addition of Gelin have been prepared:

Example 1: composition of an active toothpaste based on dicalcium phosphate.

| | |
|---|---|
| Glycerol 86% | 20 g |
| Sorbitol 70% | 10 g |
| Na—CMC | 2 g |
| Demi water | 27.5 g |
| Dicalc. Phosphate | 35 g |
| Na-dodecyl sulphate | 2 g |
| Na-saccharine | .2 g |
| Na monofluorophosphate | .2 g |
| Benzoic-acid methylester | .1 g |
| Benzoic acid propylester | .2 g |
| Flavour | 1.1 g |
| Gelin-solution | 1.8 g |
| | 100 g |

During the preparation of the toothpaste, the Gelin solution is preferably applied to the mix after all other ingredients have been added, but before the flavour is added.

Example 2: composition of an active toothpaste based on silica.

| | |
|---|---|
| Silicas, abrasive | 8 g |
| Silicas, thickening | 10 g |
| Sorbitol, 70% | 68 g |
| Na-fluoride | .2 g |
| Na-lauryl sulphate | 1 g |
| CMC | .4 g |
| Polyethylene glycol | 4 g |
| Gelin solution | 1.7 g |
| Preservatives, flavour | q.s |
| Water to 100% | |
| Example for a mouthwash: | |
| Ethyl-alcohol | 4 g |
| Flavour | 2 g |
| Gelin solution | 2.5 g |
| Demi water to 100% | |
| Example for an irrigation-liquid: | |
| Ethyl-alcohol | 5 g |
| Gelin solution | 3 g |
| Anionic surfactant | 1 g |
| Freshly boiled water to 100% | |

The solution as described earlier herewith the examples of application is obtained by dissolving the lyophilized dry GELIN in an aqueous buffer system of between pH 5 and 8.5. P-benzoic acid methylester or propylester at a dosage of 0.1% b.w. can be added for preservation.

The concentration of the Gelin in the solution is between 0.2 to 5 mg, preferably between 0.2 and 2 mg in 10 ml of a solution.

Example for a pharmaceutical composition in an aqueous form, containing GELIN

1. Dissolve Gelin in an aqueous buffer solution of pH 5 to 8.5 at a concentration of 0.5 mg/10 ml.
2. Add 0.1% b.w. para-hydroxybenzoic acid methylester.

This preparation can be used, after sterilisation through ultrafiltration for:
a. intravenous administration;
b. in an atomiser for inhalers.

Example for a pharmaceutical composition as a fatty ointment containing GELIN

1. Suspend GELIN in a suitable fatty base.
2. Add a surface active ingredient, e.g. glycerol monostearate.
3. Add 0.1% b.w. para-hydroxybenzoic acid methylester.

Both examples for pharmaceutical composition can contain further ingredients for the stabilisation of the base preparation.

The Use of Eglin in cosmetic preparations, a.o. toothpastes

The examples mentioned for both toothpaste preparations as well as the mouth preparation are similar but with the replacement of GELIN by Eglin.

The cosmetic application of Eglin in cosmetic creams is similar to the description of the preparation of a pharmaceutical composition, but for the replacement of GELIN by Eglin. Furthermore, this is used uniquely for cosmetic uses under current law.

TABLE 1

Assay conditions used to determine the inhibitory potency of gelin towards various serine proteases

| Enzyme | Buffer | Substrate | Enzyme conc. | Substrate conc. |
|---|---|---|---|---|
| Cathepsin G | 0.1M Hepes pH 7.4 | Succ—Ala—Ala—Pro—Phe—pNA | 16 nM | 2.0 mM |
| Trypsin | 0.1M Tris/HCl pH 8.0 | Bz—Arg—pNA | 50 nM | 0.8 mM |
| Chymotrypsin | 0.1M Tris/HCl + 0.96M NaCl pH 8.3 | MeO—Suc—Arg—Pro—Tyr—pNA | 16 nM | 2.4 mM |
| Elastase | 0.1M Tris/HCl + 0.05% Triton X-100, pH 8.3 | Succ—Ala—Ala—Ala pNA | 330 nM | 0.55 mM |
| Thrombin | 0.1M Tris/HCl + 0.3M NaCl pH 8.4 | Phe—Pip—Arg—pNA | 5 nM | 0.08 mM |

TABLE 2

COMPARISON OF THE AMINO ACID COMPOSITION OF GELIN AND EGLIN

Purified Gelin was hydrolysed with 6N HCl for 24 and 48 hrs and analysed for amino acid composition. The values calculated are based on an assumed molecular weight of 8100 daltons

| Amino acid | Gelin 24 hr moles/mole | Gelin 48 hr moles/mole | Eglin c* |
|---|---|---|---|
| Asp (+ Asn) | 14–15 | 19 | 7 |
| Glu (+ Gln) | 6 | 9 | 7 |
| Ser | 4 | 3–4 | 3 |
| Thr | 2–3 | 3 | 5 |
| Gly | 8–9 | 7 | 5 |
| Ala | 7–8 | 7 | 1 |
| Arg | 2 | 2 | 4 |
| Pro | 6 | 4–5 | 6 |
| Val | 11–12 | 8 | 11 |
| Met | 1 | 2 | |
| Ile | 2–3 | 2 | 0 |
| Leu | 4–5 | 3–4 | 5 |
| Phe | 2 | 2 | 5 |
| Cys | | | |
| Lys | 5–6 | 5 | 2 |
| His | 0 | 0 | 3 |
| Tyr | 1 | 0 | 5–6 |
| Trp | N.D. | N.D. | 0–1 |
| N-terminus | Val | Val | Thr |
| Total | 75–83 | 76–79 | 69–71 |

*Values obtained from ref (1)
N.D. = not determined

TABLE 3

COMPARISON OF THE N-TERMINAL SEQUENCE OF GELIN AND EGLIN

|  | 1 |  |  |  | 5 |  |  |  |  | 10 |  |  |  |  | 15 |
|---|---|---|---|---|---|---|---|---|---|---|---|---|---|---|---|
| Eglin | Thr | Glu | Phe | Gly | Ser | Asn | Leu | Lys | Ser | Phe | Pro | Asn | Val | Val | Gly |
| Gelin | Val | Asp | Glu | Lys | Ala | Glu | Val | Thr | Asp | Gly | Leu | Cys | Gly | Asp | Trp |

|  | 16 |  |  |  | 20 |  |  |  |  | 25 |  |  |  |  | 30 |
|---|---|---|---|---|---|---|---|---|---|---|---|---|---|---|---|
| Eglin | Lys | Thr | Val | Asp | Asn | Ala | Arg | Glu | Tyr | Phe | Thr | Leu | His | Tyr | Pro |
| Gelin | Thr | Cys | Ser | Gly | Ala | Gln | Val | Xaa | Gln | Asn | Asp | Ala | Ala | Val | |

TABLE 4

Sequence of peptide fragments

Sequence of peptide fragments generated after cleavage of Gelin with V8 protease or trypsin V8 fragments: peaks from separation profile in FIG. 10
peak 2:
Asn—Asp/Gly/Val—Asn/Thr—Gly—Tyr—Asp—Xaa—Xaa—Ala peak 4:
Asn—Phe—Ala/Asp—Glu peak 5:
Glu—Val—Gln—Asp—Glu peak 11:
Ala—Val—Val—Met—Ser—Pro—Val—Arg—Met peak 13:
Asn/Ser—Val—Thr—Asp—Tyr—Xaa—Val—Ser—Asp—Met—Thr Tryptic fragments, from separation profile in FIG. 8.
peak 2:

TABLE 4-continued

Sequence of peptide fragments

Ala—Glu—Val—Thr—Asp—Gly—Leu—Cys—Thr—Asp

We claim:
1. A substantially purified polypeptide having the following amino acid sequence:

```
 1            5              10             15
Val Asp Glu Ala Glu Val Thr Asp Gly Leu Cys Gly Asp Trp
        20              25
Thr Cys Ser Gly Ala Gln Val Xaa Gln Asn Asp Ala Ala Val
``` wherein Xaa indicates any amino acid residue; or a pharmaceutically acceptable salt thereof.

2. A polypeptide according to claim 1, wherein the polypeptide is an N-terminal polypeptide.

3. A polypetide according to claim 1, wherein the polypeptide has an isoelectric point of about 4.6 and substantially retains its anti-elastase activity after incubation at 100° C. for 30 minutes.

4. A pharmaceutical formulation comprising a polypeptide according to claim 1, in an elastase inhibitory amount, together with a pharmaceutically acceptable carrier, diluent or excipient.

5. A formulation according to claim 4, wherein about 20 mg of said polypeptide are dissolved in about 8 ml of an aqueous carrier, diluent or excipient.

6. A formulation according to claim 4, wherein said aqueous carrier, diluent or excipient includes glycerol.

7. A formulation according to claim 4, wherein said formulation further comprises carboxy-methyl cellulose.

8. A formulation according to claim 4, wherein said formulation is a toothpaste formulation.

9. A formulation according to claim 4, wherein said formulation is a mouthwash formulation.

10. A method of treatment of periodontal disease, which comprises administering a formulation according to claim 4 to the periodontal pocket region of a patient.

11. A method according to claim 10, wherein said periodontal disease is gingivitis.

12. A method according to claim 10, wherein about 0.05 ml of said formulation is administered to a periodontal pocket of said patient.

13. A method of inhibiting elastase activity of a bacterial source, which comprises contacting said source with a polypeptide according to claim 1 in an amount sufficient to inhibit elastase activity.

14. A method according to claim 13, wherein said bacterial source is *A. hydrophila*.

* * * * *